United States Patent
Jensen et al.

(10) Patent No.: US 10,806,432 B2
(45) Date of Patent: Oct. 20, 2020

(54) ROW-COLUMN ADDRESSED ARRAY WITH N ROWS AND N COLUMNS AND WITH LESS THAN 2N ELECTRICAL CONNECTIONS

(71) Applicant: B-K Medical Aps, Herlev (DK)

(72) Inventors: Jorgen Arendt Jensen, Horsholm (DK); Hamed Bouzari, Copenhagen (DK); Mathias Engholm, Copenhagen (DK); Erik Vilain Thomsen, Lynge (DK); Matthias Bo Stuart, Horsholm (DK)

(73) Assignee: B-K Medical ApS, Herlev (DK)

( * ) Notice: Subject to any disclaimer, the term of this patent is extended or adjusted under 35 U.S.C. 154(b) by 804 days.

(21) Appl. No.: 15/468,715

(22) Filed: Mar. 24, 2017

(65) Prior Publication Data

US 2018/0271493 A1 Sep. 27, 2018

(51) Int. Cl.
*A61B 8/00* (2006.01)
*G01S 15/89* (2006.01)
*B06B 1/02* (2006.01)

(52) U.S. Cl.
CPC ............ *A61B 8/4494* (2013.01); *A61B 8/54* (2013.01); *B06B 1/0215* (2013.01); *G01S 15/8925* (2013.01); *A61B 8/4488* (2013.01); *B06B 2201/20* (2013.01)

(58) Field of Classification Search
CPC ....... A61B 8/4494; A61B 8/54; A61B 8/4488; B06B 1/0215; B06B 2201/20; G01S 15/8925
See application file for complete search history.

(56) References Cited

U.S. PATENT DOCUMENTS

| | | | |
|---|---|---|---|
| 5,622,177 A | 4/1997 | Breimesser et al. | |
| 8,795,182 B2 | 8/2014 | Shafir et al. | |
| 10,330,781 B2* | 6/2019 | Christiansen | ......... G01S 5/8927 |
| 2007/0161899 A1 | 7/2007 | Barnes et al. | |

(Continued)

OTHER PUBLICATIONS

Morton and Lockwood, Theoretical Assessment of a Crossed Electrode 2-D Array for 3-D Imaging, 2003 IEEE Ultrasonics Symposium-968-971.

(Continued)

*Primary Examiner* — Joel Lamprecht
(74) *Attorney, Agent, or Firm* — Anthony M. Del Zoppo, III; Daugherty & Del Zoppo Co., LPA

(57) ABSTRACT

An ultrasound imaging system includes a transducer array. The array is configured for row-column addressing. The array of transducer elements includes a plurality of first 1-D arrays and a plurality of second 1-D arrays, which is orthogonal to the plurality of first 1-D arrays. The array of transducer elements further includes a plurality of front-end circuits. A single front-end circuit of the front-end circuits is in electrical communication with a single pair of 1-D arrays, which consists of a first 1-D array of the plurality of first 1-D arrays and a second 1-D array of the plurality of second 1-D arrays. The first and second 1-D arrays are either separate sets of 1-D arrays or part of a same 2-D array. In one instance, for N rows and N columns, a number of electrical connections between the elements and front-end electronics are less than 2N.

20 Claims, 5 Drawing Sheets

(56) References Cited

U.S. PATENT DOCUMENTS

2009/0096327 A1  4/2009  Kristoffersen
2015/0023135 A1  1/2015  Yuchi et al.

OTHER PUBLICATIONS

Daher, Nadim M., Rectilinear 3-D Ultrasound Imaging Using Synthetic Aperture Techniques, 2004 IEEE International Ultrasonics, Ferroelectrics and Frequency Control Joint 50th Anniversary Conference, p. 1270-1273.

Demore, Christine E.M., et al., Real-Time Volume Imaging Using a Crossed Electrode Array, 2009 IEEE Ultrasonics, vol. 56, No. 6, Jun. 2009, p. 1252-1261.

Smith, S.W., High-Speed Ultrasound Volumetric Imaging System—Part I: Transducer Design and Beam Steering, IEEE Ultrasonics, vol. 38, No. 2, Mar. 1991, p. 100-108.

Von Ramm, O.T., et al., High-Speed Ultrasound Volumetric Imaging System—Part II: Parallel Processing and Image Display, IEEE Ultrasonics, vol. 38, No. 2, Mar. 1991, p. 109-115.

Yen, J.T., et al., A Dual-Layer Transducer Array for 3-D Rectilinear Imaging, IEEE Ultrasonics, vol. 56, No. 1, Jan. 2009, p. 204-212.

\* cited by examiner

US 10,806,432 B2

ROW-COLUMN ADDRESSED ARRAY WITH N ROWS AND N COLUMNS AND WITH LESS THAN 2N ELECTRICAL CONNECTIONS

TECHNICAL FIELD

The following generally relates to ultrasound imaging and more particularly to a row-column addressed array N rows and N columns and with less than 2N electrical connections.

BACKGROUND

A two-dimensional (2-D) ultrasound transducer array includes a matrix of transducing elements. In one configuration, the elements are individually addressed. In another configuration (row-column addressing), the elements are group-wise addressed as individual rows and individual columns, where each row of elements acts as a larger single element, and each column of elements acts as a larger single element. With individual element addressing, an N×N array would require $N^2$ front-end circuits and channels to fully address all of the $N^2$ elements. For separate row and column addressing, an N×N array would require 2N front-end circuits and channels to fully address all of the N rows and all of the N columns. In either instance, however, there are practical challenges in producing the $N^2$ and 2N interconnects, and sampling and real-time processing of the data. Furthermore, the front-end circuits consume power and dissipate heat. Furthermore, the cable from the transducer to the scanner needs to house the $N^2$ (individual element addressing) or the 2N (row-column addressing) channels.

SUMMARY

Aspects of the application address the above matters, and others.

In one aspect, an ultrasound imaging system includes a transducer array. The array is configured for row-column addressing. The array of transducer elements includes a plurality of first 1-D arrays and a plurality of second 1-D arrays, which is orthogonal to the plurality of first 1-D arrays. The array of transducer elements further includes a plurality of front-end circuits. A single front-end circuit of the front-end circuits is in electrical communication with a single pair of 1-D arrays, which consists of a first 1-D array of the plurality of first 1-D arrays and a second 1-D array of the plurality of second 1-D arrays.

In another aspect, an ultrasound imaging system includes an array of transducer elements configured for row-column addressing. The array comprises a plurality of first 1-D arrays and a plurality of second 1-D arrays, which is orthogonal to the plurality of first 1-D arrays. The array further comprises a plurality of front-end circuits. A single front-end circuit of the front-end circuits is in electrical communication with a single pair of a first 1-D of the plurality of first 1-D arrays and a second 1-D array of the plurality of second 1-D arrays. The ultrasound imaging system further includes transmit circuitry electrically connected to the plurality of front-end circuits. The ultrasound imaging system further includes receive circuitry electrically connected to the plurality of front-end circuits.

In another aspect, a method includes acquiring ultrasound data with a —column addressed transducer array, beamforming ultrasound data to create an image, and displaying the image. The row-column addressed transducer array comprises a plurality of first 1-D arrays and a plurality of second 1-D arrays, which is orthogonal to the plurality of first 1-D arrays. The array of transducer elements further includes a plurality of front-end circuits. A single front-end circuit of the front-end circuits is in electrical communication with a single pair of a first 1-D of the plurality of first 1-D arrays and a second 1-D array of the plurality of second 1-D arrays.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
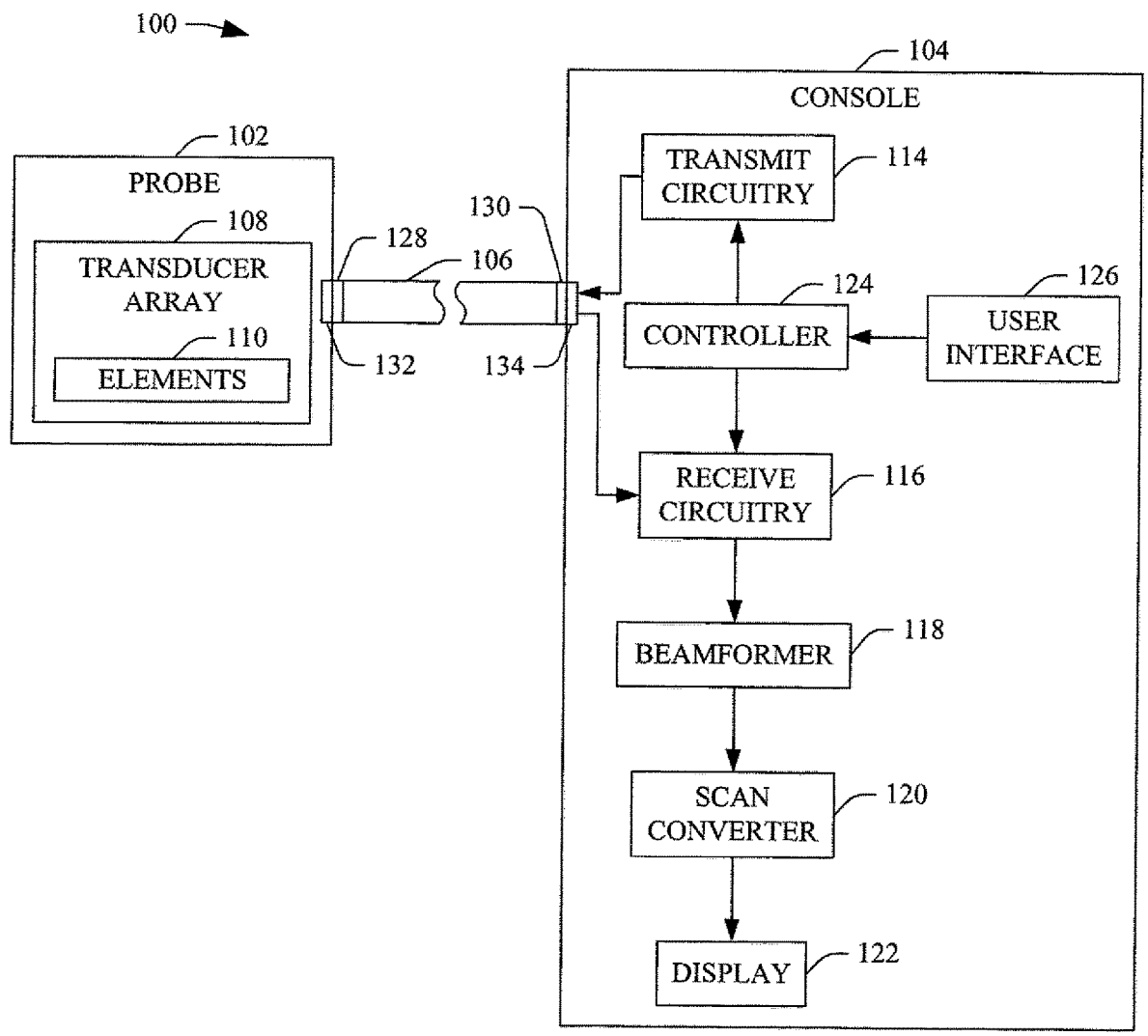
FIG. 1 schematically illustrates an example imaging system in accordance with an embodiment described herein.

FIG. 1 schematically illustrates an example imaging system 100 including an ultrasound imaging system. The illustrated ultrasound imaging system includes a probe 102 and a console 104. The probe 102 and the console 104 electrically communicate via a communication channel 106.

The probe 102 includes a transducer array 108 of transducer elements 110. In one instance, the transducer array 108 includes a 2-D array and the elements 110 are spatially arranged as a N×M matrix of N rows and M columns, where N and M are positive integers, and N=M or N≠M (e.g., N>M or N<M). Examples of square arrays include 64×64, 192×192, 256×256, 512×512 and/or other arrays, including larger and/or smaller arrays. Examples of suitable array also include rectangular, circular, irregular and/or other shaped arrays. In another instance, the transducer array 108 includes separate sets of 1-D arrays (1-D row arrays and 1-D column arrays) of the elements 110 (e.g., in different layers), each of length N or M. Examples of arrays include 64, 192, 256, 512 and/or other arrays, including larger and/or smaller arrays. The elements 110 can be piezoelectric (PZT), capacitive micromachined ultrasonic transducer (CMUT) elements, and/or other transducing elements.

Figure 2:
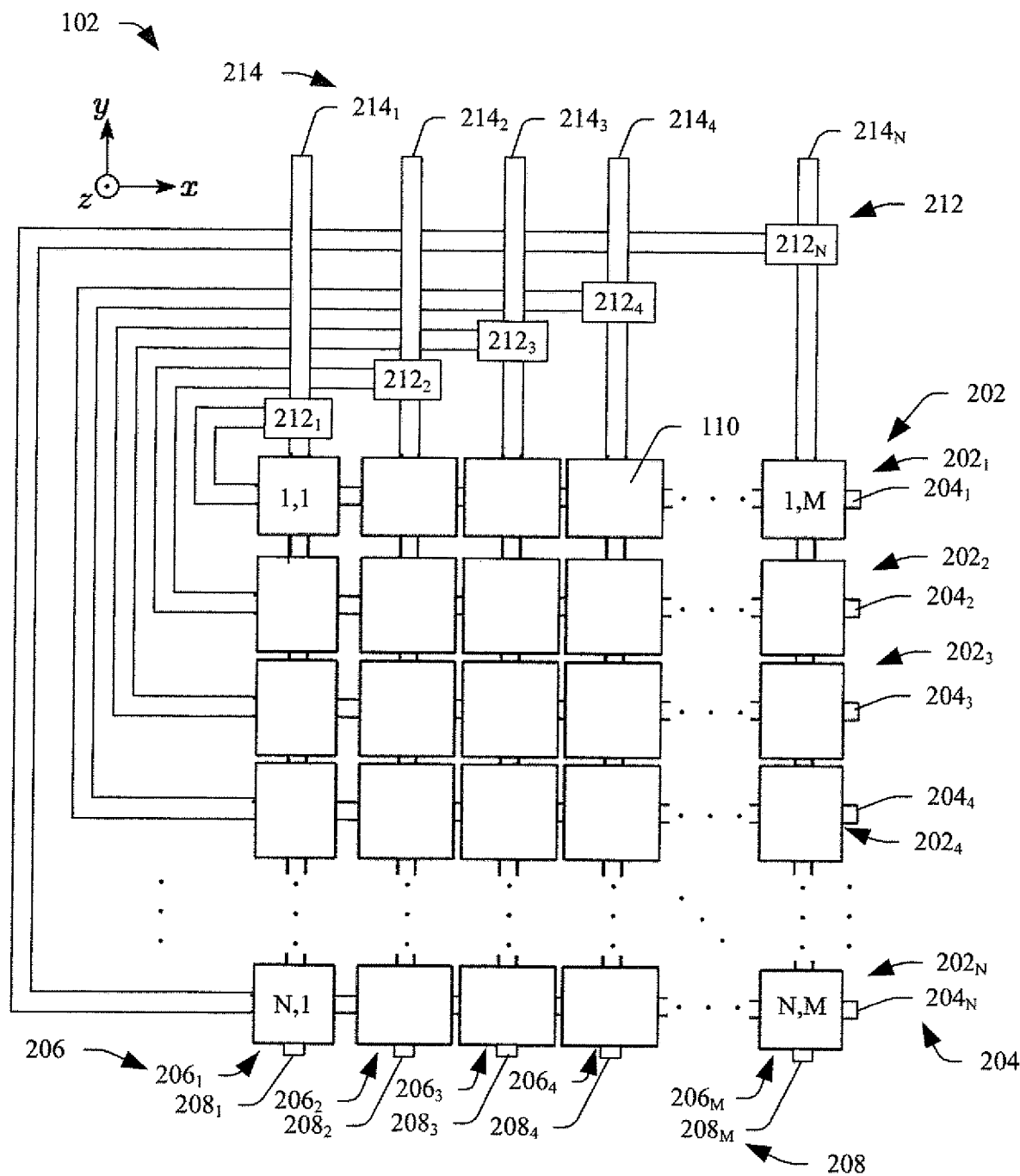
FIG. 2 schematically illustrates an example 2-D array of the imaging system in accordance with an embodiment described herein.

In the illustrated embodiment, the transducer elements 110 are configured for row-column addressing. With a 2-D array, row-column addressing effectively transforms the N×M element 2-D array into two 1-D arrays, one with N 1-D arrays and the other with M 1-D arrays, which are orthogonal to the N 1-D arrays. FIG. 2 schematically illustrates an example 2-D transducer array where N=M. In FIG. 2, each of N rows 202 ($202_1, \ldots, 202_M$) includes an electrically conductive trace 204 ($204_1, \ldots, 204_M$) in electrical communication with each element 110 of the corresponding row 202. Each of M columns 206 ($206_1, \ldots, 206_M$) includes an electrically conductive trace 208 ($208_1, \ldots, 208_M$) in electrical communication with the elements 110 of the responding column 206.

In the example in FIG. 2, the elements 110 of the columns 206 are arranged in a first or "y" direction of an "x-y" plane, and the elements 110 of the rows 202 are arranged in a second or "x" direction of the "x-y" plane. The elements 110 are configured to transmit ultrasound signals in response to being excited by an electrical signal or pulse. The elements 110 are also configured to receive echoes (echo signals) and generate electrical signals indicative of the received echo signals. An echo, generally, is a result of the interaction between a transmitted ultrasound signal and static and/or moving structure, such as organ cells, soft tissue, flowing blood cells in a vessel, etc.

With row-column addressing, the rows 202 or the columns 206 transmit creating a line focus of the transmit pulse, and the columns 206 or the rows 202 receive enabling receive focus. The combination of transmit and receive focus provides focusing on a point in the volume, hence a volumetric image can be created. In one instance, both the rows 202 and the columns 206 can be used interchangeably as either transmitters or receivers. This includes emitting with rows and receiving with columns, emitting with rows and receiving with rows, emitting with columns and receiving with rows, and/or emitting with columns and receiving with columns. This can be achieved via one element transmitting and receiving with all elements, multiple elements transmitting (e.g., focused or defocusing beam) and receiving with all elements, all elements transmitting and receiving with all elements.

In the illustrated embodiment, pairs of rows 202 and columns 206 share front-end circuits 212. For example, a row $202_1$ and a column $206_1$ share a front-end circuit $212_1$, a row $202_2$ and a column $206_2$ share a front-end circuit $212_2$, a row $202_3$ and a column $206_3$ share a front-end circuit $212_3$, a row $202_4$ and a column $206_4$ share a front-end circuit $212_4, \ldots$, and a row $202_M$ and a column $206_N$ share a front-end circuit $212_N$. The front-end circuits 212 switch between the transmitting rows 202 (or columns 206) and the receiving columns 206 (or rows 202), and between transmitting with the row 202 and receiving with the columns 206 and vice versa.

As described in greater detail below, this configuration described herein includes N the front-end circuits 212 and N channels 214 ($214_1, \ldots, 214_N$) therefrom to the console 104 via the communication channel 106. As such, the approach described herein has half the number of front end circuits and channels (e.g., in a handle portion of the probe 102) relative to a configuration in which each of the rows 202 and the columns 206 includes its own front-end circuit 212 and channel 214, which would require 2N front-end circuits and channels. As such, power consumption, heat dissipation, and cable cost are less than that of the configuration with the 2N front-end circuits and channels.

In one instance, the reduction in the number of the front-end circuits 212 and the channels 214 (from 2N to N) to the console 104 does not compromise image quality or frame rate. Furthermore, the reduction in the number of the front-end circuits 212 and the channels 214 for each pairs of rows 202 and columns 206 allows for quadrupling the number of elements 110 while maintaining the same number of front end circuits and channels as the configuration where each row and column has its own front end circuit and channel. Alternatively, the number of elements 110 can be increased while the number of front end electronics circuits and connections are decreased.

Returning to FIG. 1, the console 104 includes transmit circuitry 114, which is configured to generate pulses that excite a predetermined set of the addressed columns 206 (or the rows 202) to emit one or more ultrasound beams or waves. Receive circuitry 116 receives the signals generated by the rows 202 (or the columns 206). The receive circuitry 116 may also pre-process and/or condition the received signals, e.g., by amplifying, digitizing, etc. the signals.

A beamformer 118 processes the received echoes, e.g., by applying time delays and weights, summing, and/or otherwise processing the received echoes. A scan converter 120 scan converts the beamformed data, converting the beamformed data (e.g., images or volumes) into the coordinate system of a display 122, which visually displays the images. In one instance, the data is visually displayed in an interactive graphical user interface (GUI), which allows the user to selectively rotate, scale, and/or manipulate the displayed data through a mouse, a keyboard, touch-screen controls, etc.

A controller 124 controls one or more of the components of the console 104. Such control can be based on the mode of operation (e.g., B-mode, etc.) of the system 100 and/or otherwise. A user interface 126 includes an input device (e.g., a physical control, a touch-sensitive surface, etc.) and/or an output device (e.g., a display screen, etc.). An imaging mode, scanning, and/or other function can be activated by a signal indicative of input from the user interface 126.

In one instance, the communication channel 106 includes a cable which houses, supports and routes the channels 214 and includes electro-mechanical interfaces 128 and 130 on each end. The electro-mechanical interfaces are 128 and 130 configured to electrically and mechanically interface with complementary electro-mechanical interfaces 132 and 134 of the probe 102 and the console 104. One or more of the electrically and mechanically interfaces is either statically fixed to its complementary electro-mechanical interface or removeably coupled to its complementary electro-mechanical interface. In another instance, the communication channel 106 is a wireless channel (e.g., radio frequency (RF), etc.).

In one embodiment, the console 104 is part of a computing device such as a laptop computer.

In another embodiment, the console 104 is statically or removeably coupled to a mobile or portable cart system with wheels, casters, rollers, or the like, which can be moved around. In this instance, the display 122 may be separate from the console and connected thereto through a wired and/or wireless communication channel. Where the cart includes a docking interface, the console can be interfaced with the cart and used. An example of such a system is described in US publication 2011/0118562 A1, entitled "Portable ultrasound scanner," and filed on Nov. 17, 2009, which is incorporated herein in its entirety by reference.

In another embodiment, the probe 102 and the console 104 and the components thereof are integrated in or are part of a hand-held ultrasound apparatus, which includes a housing that mechanically supports and/or shields the components, where the transducer array 108, the user interface 126 and/or the display 122 are structurally integrated as part of the housing. An example of a hand-held device is described in U.S. Pat. No. 7,699,776, entitled "Intuitive Ultrasonic Imaging System and Related Method Thereof," and filed on Mar. 6, 2003, which is incorporated herein in its entirety by reference.

In a variation, the console 104 further includes a velocity processor configured to process data generated by the beamformer 118 to produce 3-D vector flow data, including an axial component, a first lateral component transverse to the axial component, and a second lateral component transverse to the axial component and the first lateral component. Examples of the velocity processor are described in application Ser. No. 12/599,857, filed Jan. 19, 2015, and entitled "3-D Flow Estimation using Row-Column addressed transducer arrays," and application number PCT/IB2016/056817, filed Nov. 11, 2016, and entitled "3-D Imaging and/or Flow Estimation with a Row-Column Addressed 2-D Transducer Array," the entirety of both are incorporated herein by reference.

Figure 3:
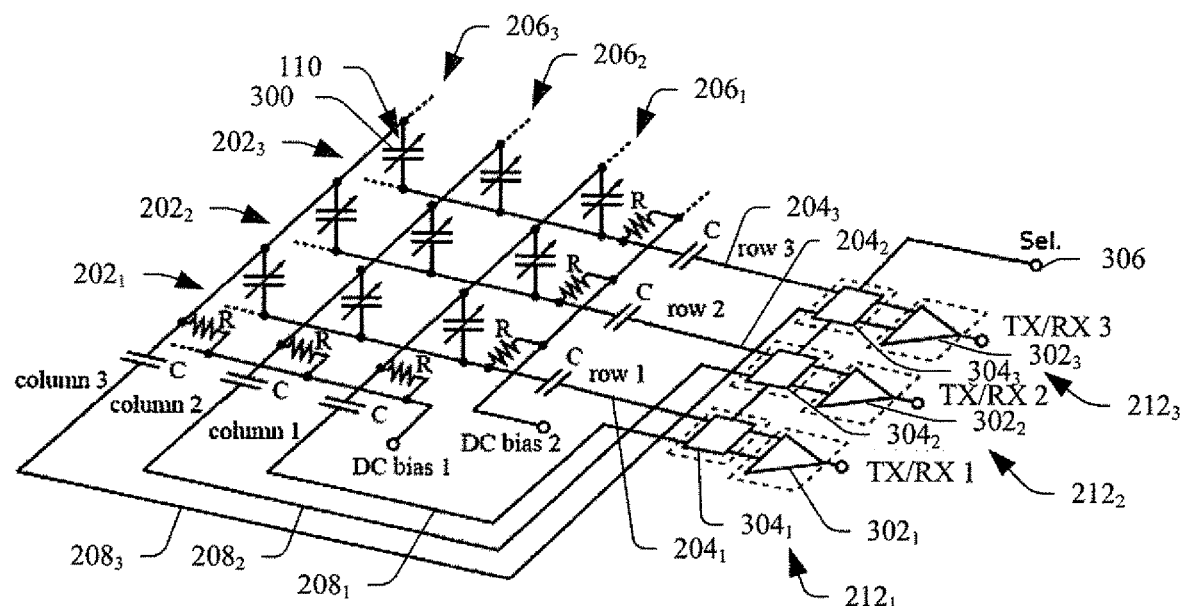
FIG. 3 schematically illustrates an example of front-end circuits and channels of the 2-D array in accordance with an embodiment described herein.

FIG. 3 schematically illustrates an embodiment of the shared front-end circuits 212 for three of the rows 202 and three of the columns 206 of the example of FIG. 2. The shared front-end circuits 212 can also be used with a configuration in which the array 108 includes separate 1-D arrays instead of the 2-D array.

In this example, the elements 110 include CMUTs, which are represented as variable capacitors 300. Each of the column channels $208_1$, $208_2$, and $208_3$ is in electrical communication, via respective CMUTs 110 of the columns $206_1$, $206_2$, and $206_3$, to all row channels 204, and vice versa. Direct current (DC) biases are low-pass filtered through resistors (R's) (e.g., one megaohm (1 M Ω) resistors) in conjunction with the CMUTs 110. Alternating current (AC) signals to and from the CMUTs 110 are high-pass filtered with capacitors (C's) (e.g., ten nanofarad (10 nF) together with the resistors R. Where the elements 110 include piezoelectric elements, the resistors and capacitors are omitted.

In this example, the front-end circuits $212_1$, $212_2$, and $212_3$ include pre-amplifiers $302_1$, $302_2$, and $302_3$ in electrical communication with switches $304_1$, $304_2$, and $304_3$. The pre-amplifiers $302_1$, $302_2$, and $302_3$ respectively are also in electrical communication with electrical pathways TX/RX 1, TX/RX 2, and TX/RX 3 to the transmit circuitry 114 (FIG. 1) and the receive circuitry 116 (FIG. 1). The switches $304_1$, $304_2$, and $304_3$ respectively are also in electrical communication with channel pairs $204_1/208_1$, $204_2/208_2$, and $204_3/208_3$. A select contact or electrode 306 controls the switches $304_1$, $304_2$, and $304_3$, as described below.

Figure 4:
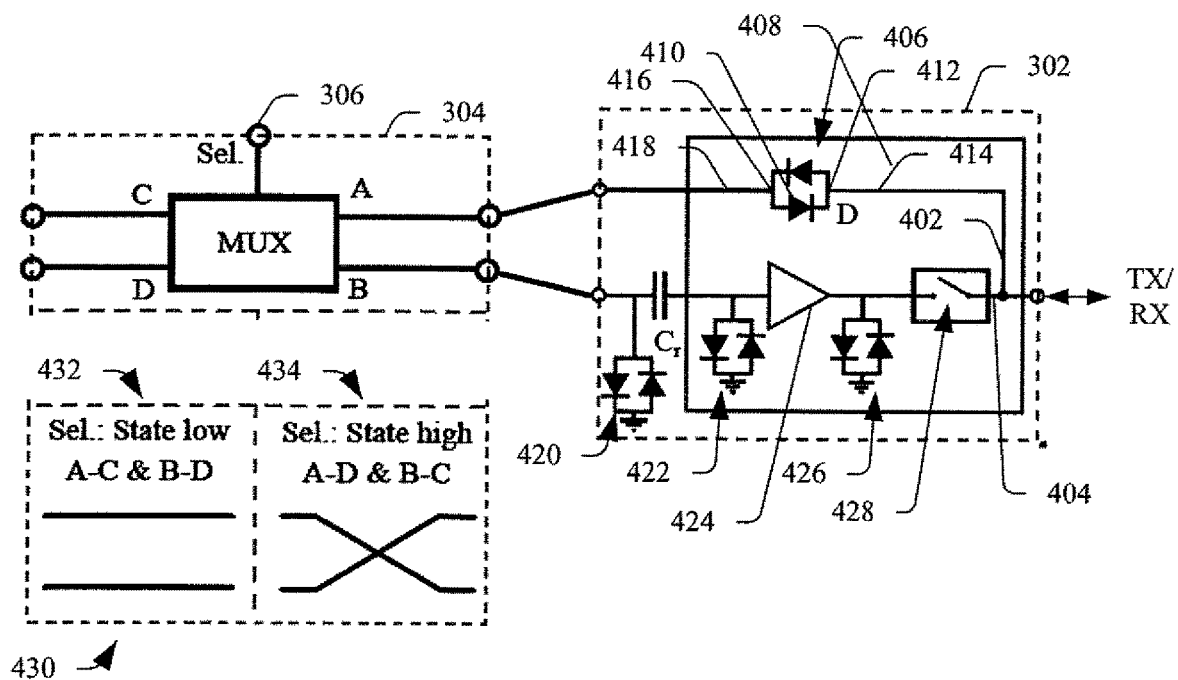
FIG. 4 schematically illustrates an example where the front-end circuits include buffer amplifiers and multiplexors.

FIG. 4 illustrates an example of the pre-amplifiers $302_1$, $302_2$, and $302_3$ and the switches $304_1$, $304_2$, and $304_3$, which are implemented through multiplexors.

In this example, the pre-amplifiers 302 includes a transmit path 402 and a receive path 404. The transmit path 402 includes a circuit 406 with anti-parallel diodes consisting of two diodes 408 and 410 in parallel in reverse direction where an anode of one of the diodes and a cathode of the other diode are electrically connected to a same junction 412 on a first leg 414 of the path 402, and a cathode of the one of the diodes and an anode of the other diode are electrically connected to a same different junction 416 on a second different leg 418 of the path 402. The anti-parallel diodes 408 and 410 pass the high voltage (hundreds of volts) signal to the multiplexor 304 and block signals in the opposite direction.

The receive path 404 includes, in order, anti-parallel diodes 420 electrically connected to electrical ground, a capacitor $C_r$, anti-parallel diodes 422 electrically connected to electrical ground, a buffer amplifier 424, anti-parallel diodes 426 electrically connected to electrical ground, and a switch 428. The anti-parallel diodes 420, 422 and 426 and the switch 428 protect the low voltage (nano-volts) receive path 402 and buffer amplifier 424 from the high voltage transmission burst. The anti-parallel diodes 420, 422 and 426 electrical short high voltage to electrical ground. The switch 428 operates automatically via sensing transmit/receive operations, or is controlled via a signal. The capacitor $C_r$ passes AC signals and blocks DC signals. The buffer amplifier 424 amplifies the received signal.

The multiplexor 304 is configured to operate alternatively in one of two states, either a pass-through state which passes a high voltage signal directly through or a cross-over state which routes the high voltage signal to another path. The multiplexor 304 includes the select electrode 306, which controls whether the multiplexor 304 operates as a pass-through or cross over. These states are shown at 430. In a low state 432, the multiplexor 304 acts as a pass-through and the signal on line A passes through to line C and the signal on line D passes through to line B. In a high state 434, the multiplexor 304 acts as a cross-over and the signal on the line A is routed to the line D and the signal on the line C is routed to the line B.

With this configuration, the signal at the select electrode 306 determines whether the rows 202 will be used to transmit and the columns 206 will be used to receive, or vice versa. The switch 428 switches between transmit and receive operations. Generally, a signal is first applied to the select electrode 306 of the multiplexor 304 to choose between the columns 204 and rows 206 for transmit. Then, the switch 428 of the pre-amplifier 302 opens for a transmit operation, and the multiplexor 304 routes the transmit signal accordingly. After the transmit operation, the switch 428 closes for a receive operation, and the multiplexor 304 routes the received signal accordingly. These acts are repeated for each transmit/receive event.

An example of suitable circuitry for the pre-amplifier 302 is the MAX4805A Octal High-Voltage-Protected, Low-Power, Low-Noise Operational Amplifier, a product of Maxim Integrated™, San Jose, Calif., USA. Other pre-amplifiers are also contemplated herein.

In a variation, the pre-amplifier 302 includes only the two paths 402 and 404, the buffer amplifier 424 and the switch 428 configured to switch between transmit and receive operations.

Figure 5:
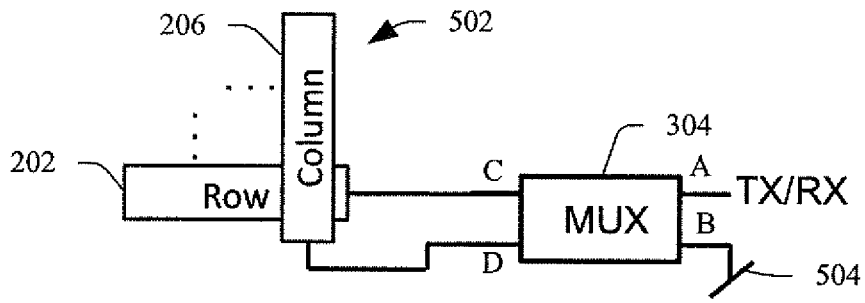
FIG. 5 schematically illustrates an example where the front-end electronics include only the multiplexors and the array includes a 2-D array.

In another variation, the front-end circuits $212_1$, $212_2$, and $212_3$ do not include pre-amplifiers $302_1$, $302_2$, and $302_3$; that is, the pre-amplifiers $302_1$, $302_2$, and $302_3$ are omitted. An example of this variation is shown in FIG. 5 for a row-column addressed 2-D array 502 where either the rows 202 or the columns 206 are used as signal electrodes, and the orthogonal columns 206 or rows 202 are electrically connected to electrical ground 504. In this embodiment, the line A of the multiplexor 304 is directly in electrical communication with the electrical pathway TX/RX to the transmit circuitry 114 (FIG. 1) and the receive circuitry 116 (FIG. 1), and the path B is at electrical ground.

For transmit on the rows 202, the select signal at the select electrode 306 places the multiplexor 304 in the low state 432 (FIG. 4) where it behaves as a pass-through which passes the transmit signal from the console 104 on the line A to the line C to the rows 202, and the columns 206 are placed at electrical ground, and then switches the multiplexor 304 to the high state 434 (FIG. 4) for receive where it behaves as a cross-over which routes the receive signal from the columns 206 on the line D to the line A, and the rows 202 are placed at electrical ground.

For transmit on the columns 206, the select signal at the select electrode 306 places the multiplexor 304 in the high state 434 (FIG. 4) where it behaves as a cross-over which routes the transmit signal from the console on the line A to the line D to the columns 206, and the rows 202 are placed at electrical ground, and then switches the multiplexor 304 to the low state 432 (FIG. 4) for receive where it behaves as a pass-through which passes the receive signal from the rows 202 on the line path C to the line A to the console 104, and the columns 206 are placed at electrical ground.

Figure 6:
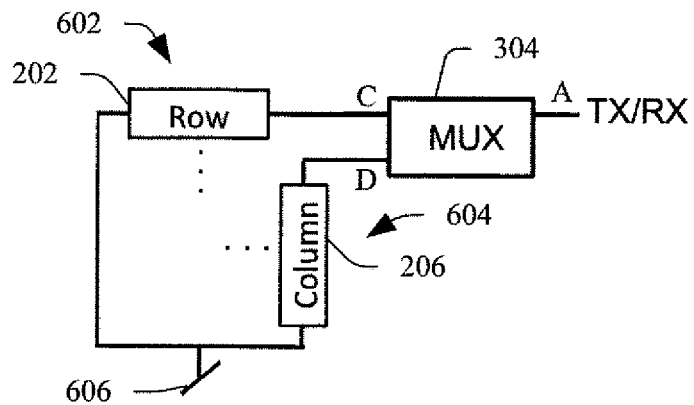
FIG. 6 schematically illustrates an example where the front-end electronics include only the multiplexors and the array includes two separate 1-D arrays.

An example of this variation is shown in FIG. 6 for row-column addressed arrays with a separate 1-D linear transducer layer 602 for the rows 202 and a separate 1-D linear transducer layer 604 for the columns 206. In this configuration, a common electrical ground 606 is between the two layers 602 and 604. I have attached a paper describing this type of row-column transducer. Two versions of the drawings have been made covering both array configurations. The application also needs to be revised to cover both types of row-column realizations.

Figure 7:
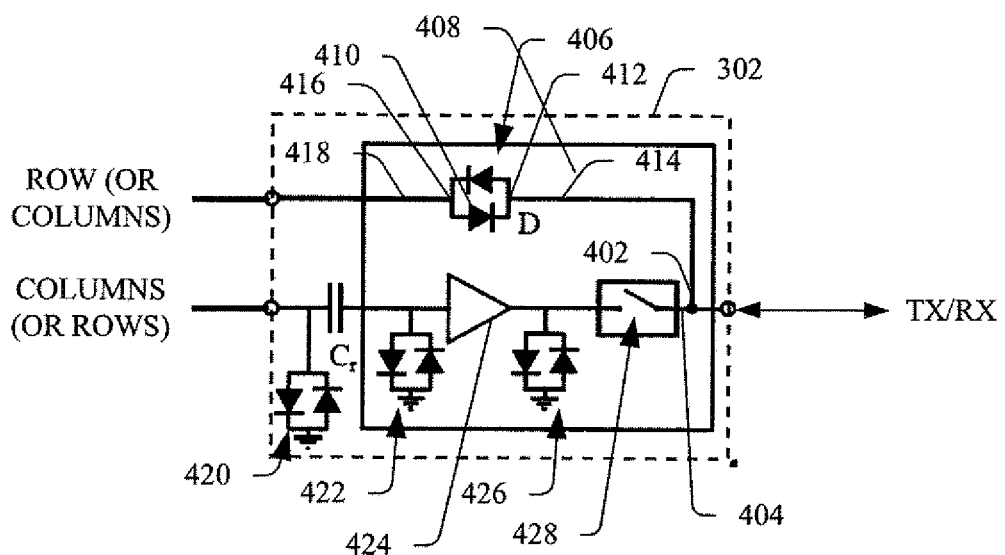
FIG. 7 schematically illustrates an example where the front-end electronics include only the buffer amplifiers.

In another variation, the switches 304 are omitted. In this configuration, only the rows 202 or the columns 206 can be used to transmit and the columns 206 or the rows 202 is used for receive. An example for this is shown in FIG. 7.

Figure 8:
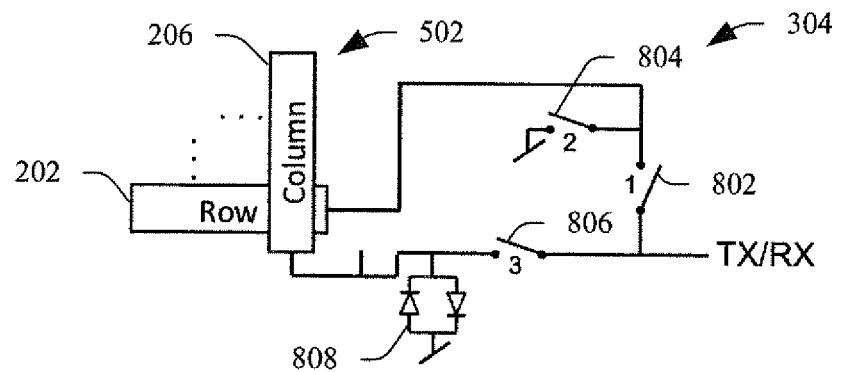
FIG. 8 schematically illustrates an example where the front-end electronics include fast switches and the array includes the 2-D array.
Figure 9:
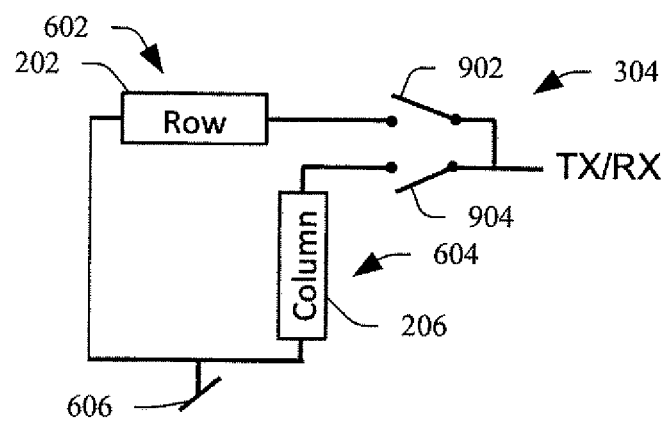
FIG. 9 schematically illustrates an example where the front-end electronics include fast switches and the array includes the two separate 1-D arrays.
Figure 10:
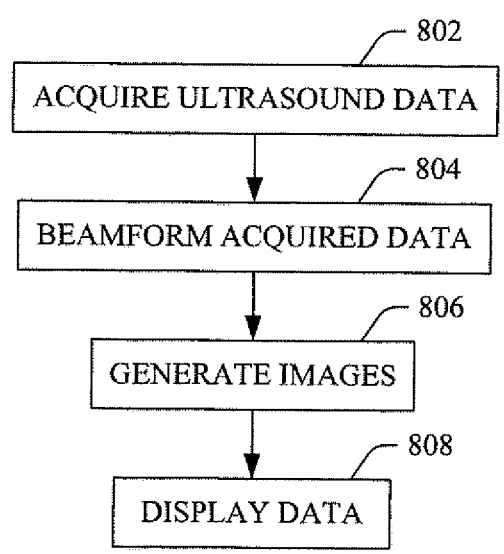
FIG. 10 schematically illustrates an example method in accordance with an embodiment described herein.

In another variation, as shown in FIG. 8 for the configuration with the 2-D array 502, fast switches 802, 804 and 806 and a pair of anti-parallel diodes 808 are employed instead of the multiplexor 304. The switches 802, 804 and 806 can be substantially similar to the switch 428 in FIGS. 4 and 7. In transmit, the switch 802 is closed and the switches 804 and 806 are open. The signal follows a signal through the switch 802 to the transducer element 110 and is connected to electrical ground via the diode pair 808. In receive, the switch 802 is open and the switches 804 and 806 are closed. The received signal is read out through the switch 806 and grounded through the switch 804. For the configuration with the two separate 1-D linear transducer layers 602 and 604, the multiplexor is replaced with fast switches 902 and 904, as shown in FIG. 9.

In one instance, where the front-end circuits and the channels are integrated in a handle of the probe 102, the lower channel count and reduced number of front-end electronics circuits renders the approach described herein well-suited for a low cost and/or wireless probe. In another instance, this also renders the approach described herein well-suited for a large probe since a four (4) times larger area is possible with the same number connections. This is especially interesting for abdominal probes, and for high frequency probes since the lower penetration depth, due to the high frequency, can be avoided by having a bigger aperture.

Two-dimensional probes using the approach described herein will require the same electronics and connections as a 1-D probe of equivalent size. Furthermore, transmission and receiving connections can be optimized separately with respect to the impedance matching. The capacitor Cr (FIG. 4) can be chosen dependent on an equivalent output impedance of the transducer. A higher capacitance value provides a lower attenuation of the received echo signal at expenses of a greater attenuation of the transmit signal. Since the transmission and receive channel are partially separated the impedance can be matched independently.

The components described herein can include discrete components, CMOS components, a combination thereof, and/or other components. For example, the front-end circuits (e.g., the buffer amplifiers and/or the switches) can be separate integrate chips (IC's) or on the CMOS chip.

FIG. 8 illustrates an example method. At 802, the controller 124 controls the transducer array 108 the transmit circuitry 114 and the receive circuitry 116 to acquire ultrasound data using row-column addressing using the transducer array 108 described herein. At 804, the acquired data is beamformed. At 806, the beamformed data is processed to generate an image. At 808, the image is displayed.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array configured for row-column addressing, wherein the array comprises:
   a plurality of first 1-D arrays; and
   a plurality of second 1-D arrays, which is orthogonal to the plurality of first 1-D arrays; and
   a plurality of front-end circuits, wherein a single front-end circuit of the plurality of front-end circuits is in electrical communication with only a single pair of 1-D arrays, which consists of a first 1-D of the plurality of first 1-D arrays and a second 1-D array of the plurality of 1-D arrays.

2. The ultrasound imaging system of claim 1, wherein the single front-end circuit comprises:
   a switch with two channels respectively electrically connected to the first 1-D and the second 1-D array of the pair.

3. The ultrasound imaging system of claim 2, wherein the single front-end circuit further comprises:
   a buffer amplifier with a transmit path, a receive path, and a transmit/receive switch; wherein the transmit path and the receive path are electrically connected to the two channels of the switch.

4. The ultrasound imaging system of claim 3, wherein the buffer amplifier comprises:
   at least one circuit configured to short transmission high voltage bursts on the receive path to electrical ground.

5. The ultrasound imaging system of claim 3, wherein the transmit/receive switch is configured to automatically switch between the transmit path and receive path between transmit and receive operations of the transducer array.

6. The ultrasound imaging system of claim 3, wherein the switch is configured to electrically connect the transmit path to either the first 1-D array or the second 1-D array and the receive path to the other of the first 1-D or the second 1-D array.

7. The ultrasound imaging system of claim 6, wherein the switch comprises:
   a select terminal configured to alternatively place the switch in a first state in which the transmit path is electrically connected to the first 1-D array and the receive path is electrically connected to the second 1-D array, and a second state in the transmit path is electrically connected to the second 1-D array and the receive path is electrically connected to the first 1-D array.

8. The ultrasound imaging system of claim 7, wherein the switch comprises:
a select terminal configured to alternatively place the switch in a first state or a second state.

9. The ultrasound imaging system of claim 2, wherein the switch, for transmit, electrically connects to only one of the first 1-D or the second 1-D array, and, for receive, electrically connects to only one of the first 1-D or the second 1-D array.

10. The ultrasound imaging system of claim 2, wherein the switch includes separate switches, one for transmit and one or receive.

11. An ultrasound imaging system, comprising:
a transducer array configured for row-column addressing, wherein the array comprises:
a plurality of first 1-D arrays; and
a plurality of second 1-D arrays, which is orthogonal to the plurality of first 1-D arrays; and
a plurality of front-end circuits, wherein a single front-end circuit of the plurality of front-end circuits is in electrical communication with only a single pair of 1-D arrays, which consists of a first 1-D of the plurality of first 1-D arrays and a second 1-D array of the plurality of 1-D arrays;
transmit circuitry electrically connected to the plurality of front-end circuits; and
receive circuit electrically connected to the plurality of front-end circuits.

12. The ultrasound imaging system of claim 11, wherein the single front-end circuit comprises:
a buffer amplifier electrically connected to the transmit circuitry and the receive circuitry; and
a switch electrically connected to the buffer amplifier and the pair of the first 1-D and the second 1-D array.

13. The ultrasound imaging system of claim 12, wherein the buffer amplifier comprises:
a transmit path;
a receive path with an amplifier; and
a transmit/receive switch configured to switch between the transmit path and the receive path respectively for transmit and receive operations.

14. The ultrasound imaging system of claim 11, wherein the switch comprises:
a multiplexor configured to electrically connect the transmit path to either the first 1-D array or the second 1-D array and electrically connect the other of the first 1-D or the second 1-D array to the receive path.

15. The ultrasound imaging system of claim 14, wherein the multiplexor comprises:
a select terminal configured to alternatively place the multiplexor in a first state in which the transmit path is electrically connected to the first 1-D array and the receive path is electrically connected to the second 1-D array, and a second state in the transmit path is electrically connected to the second 1-D array and the receive path is electrically connected to the first 1-D array.

16. The ultrasound imaging system of claim 11, wherein the single front-end circuit comprises:
a switch electrically connected to the pair of the first 1-D and the second 1-D array and the transmit circuitry and the receive circuitry.

17. The ultrasound imaging system of claim 16, wherein the switch comprises:
a multiplexor configured to electrically connect the transmit path to either the first 1-D array or the second 1-D array and electrically connect the other of the first 1-D or the second 1-D array to the receive path.

18. The ultrasound imaging system of claim 17, wherein the multiplexor, for transmit, electrically connects the transmit circuitry to only one of the first 1-D or the second 1-D, and, for receive, electrically connects the receive circuitry to the only one of the first 1-D or the second 1-D array.

19. The ultrasound imaging system of claim 17, wherein the multiplexor comprises:
a select terminal configured to alternatively place the multiplexor in a first state in which the transmit path is electrically connected to the first 1-D array and the receive path is electrically connected to the second 1-D array, and a second state in the transmit path is electrically connected to the second 1-D array and the receive path is electrically connected to the first 1-D array.

20. A method, comprising:
Acquiring ultrasound data with a row-column addressed transducer array, wherein the row-column addressed transducer array comprises:
a plurality of first 1-D arrays; and
a plurality of second 1-D arrays, which is orthogonal to the plurality of first 1-D arrays; and
a plurality of front-end circuits, wherein a single front-end circuit of the plurality of front-end circuits is in electrical communication with only a single pair of 1-D arrays, which consists of a first 1-D of the plurality of first 1-D arrays and a second 1-D array of the plurality of 1-D arrays;
beamforming ultrasound data to create an image; and
displaying the image.

* * * * *